United States Patent [19]

Zlobinsky et al.

[11] Patent Number: 5,252,485
[45] Date of Patent: Oct. 12, 1993

[54] UNIT FOR HYDROLYZING AMINO-ACID CONTAINING SPECIMENS

[75] Inventors: Yury Zlobinsky, Massapequa; Jules S. Lux, Valley Stream, both of N.Y.

[73] Assignee: Savant Instruments, Inc., Farmingdale, N.Y.

[21] Appl. No.: 565,467

[22] Filed: Aug. 10, 1990

[51] Int. Cl.⁵ .......................... C12M 1/02; C12M 1/36
[52] U.S. Cl. .................................... 435/316; 435/287; 435/289; 422/99
[58] Field of Search ........................... 422/63, 66–67, 422/99, 102, 104; 127/1; 435/287, 296, 289, 316, 809

[56] References Cited

U.S. PATENT DOCUMENTS

| | | | |
|---|---|---|---|
| 3,216,207 | 11/1965 | Boyer et al. | 422/99 |
| 3,784,343 | 1/1974 | Iwasaki | 425/405.1 |
| 3,948,733 | 4/1976 | Conkerton | 435/296 |
| 4,011,048 | 3/1977 | Johnson et al. | 422/63 |
| 4,518,335 | 5/1985 | Pujari | 425/405.1 |
| 4,666,853 | 5/1987 | Meserol et al. | 435/290 |
| 4,867,924 | 9/1989 | Schilkey et al. | 425/405.1 |
| 4,904,450 | 2/1990 | Floyd | 422/99 |
| 4,933,146 | 6/1990 | Meyer et al. | 422/104 |
| 4,944,923 | 7/1990 | Heinrichs et al. | 422/104 |
| 5,015,445 | 5/1991 | Doleman et al. | 422/104 |
| 5,016,583 | 4/1992 | Raysberg et al. | 422/102 |

FOREIGN PATENT DOCUMENTS 1-180457  7/1989  Japan .

OTHER PUBLICATIONS

"Encyclopedia of Chemical Technology" vol. 3, Edition 1, Pub. 1954, pp. 508–510.

Primary Examiner—James C. Housel
Assistant Examiner—T. A. Trembley
Attorney, Agent, or Firm—George J. Brandt, Jr.

[57] ABSTRACT

Amino acid-containing specimens are hydrolyzed with a method and in a hydrolysis unit by which a specimen holder having an upper face side against which a cover can be tightly engaged to seal compartments formed in the holder and define a sample chamber in which the specimens are received and hydrolyzed. The holder and cover are housed in a sealable casing, and a heating device is provided to apply heat to the specimens while same are in contact with a hydrolyzing agent, this being done while the casing is sealed from the ambient atmosphere and the holder compartments in turn sealed from the casing enclosed space. The unit embodies a device to impose vacuum on the casing interior during the hydrolysis cycle, or to fill the casing enclosed space with an inert gas for cooling at the end of hydrolysis. The sealable nature of the holder compartments and casing interior facilitates pre and/or post-hydrolysis cleaning and purging of the holder compartments to insure specimen contamination avoidance during hydrolysis. Structure is provided to cool down the specimen holder on completion of a hydrolysis cycle to shorten the overall hydrolysis procedure and facilitate further handling of the hydrolyzed specimens as well as early reuse of the unit for further hydrolysis operation.

41 Claims, 7 Drawing Sheets

UNIT FOR HYDROLYZING AMINO-ACID CONTAINING SPECIMENS

BACKGROUND OF THE INVENTION

The present invention relates to a hydrolysis unit with which amino-acid-containing specimens such as proteins, peptides and the like can be hydrolyzed to break down the speciments into their amino acids thereof, as well as to a method for hydrolyzing such specimens.

Amino acid analysis, i.e., determining the amino acid content of biological samples is widely practiced in biological research and biotechnology. It also is commonly utilized in forensics and in the food industry where it has importance in nutritional analysis of both human and animal foodstuffs. Generally, hydrolysis will be effected by contacting specimens with a hydrolyzing agent such as hydrochloric acid in the presence of heat to cause a protein or peptide to break down into its component amino acids.

In the hydrolysis operation, care must be exercised to avoid contamination and other adverse alteration of specimen character, particularly because a peptide, for example, which is being analyzed may constitute a presence of only a few nanograms so that loss of some such presence may be fatal to the desired analysis. Further, certain samples may not be replaceable so that an intended and needed analysis is not possible.

Contamination can occur for various reasons including improper washing of glassware, improper specimen handling, atmospheric dust as well as other causes. Also, the hydrolysis apparatus itself can cause contamination such as aluminum salts a common component in borosilicate glass hydrolysis vessels, can react with the specimen during hydrolysis. Presence of oxygen during high-temperature hydrolysis can denature or destroy amino acids, and this has led to the need to hydrolyze in a vacuum or inert atmosphere.

Another hazard is possible sample loss when specimens are handled and moved from a concentration operation to the hydrolysis operation.

Various apparatus and hydrolyzing techniques have been used heretofore, but these do not lend themselves in practice to simple, easily fulfilled hydrolyzing wherein maximized elimination of contamination is achieved. Nor due such prior techniques and apparatus represent ways to obtain higher temperature hydrolysis coupled with higher productivity, safety of operation and consistency of results as is thought desirable and which is made possible by the method and hydrolysis unit of the present invention.

OBJECTS AND SUMMARY OF THE INVENTION

Accordingly, it is an object of the invention to provide a hydrolysis unit and method for hydrolyzing amino acid-containing specimens which overcomes the drawbacks of the prior art.

It is a further object of the invention to provide a hydrolysis unit which allows hydrolyzing amino acid-containing specimens at various temperatures and for various time periods leading to capacity for more versatility in effecting amino acid analyses.

It is a still further object of the invention to provide a hydrolysis unit and hydrolysis method with which hydrolysis of amino acid-containing specimens can be carried out with little likelihood that specimen contamination will, or because of the particularized and preventative hydrolyzing procedures employed, can occur during the hydrolyzing cycle.

Another object is to provide a hydrolysis unit that allows achieving more consistency in results in the hydrolysis of amino acid-containing specimens.

A still further object is to provide a hydrolysis unit which offers in use, maximized protection to workers from any accidental happening involving hydrolyzing agent and/or specimen escape from the unit.

Yet another object is to provide a hydrolysis unit which employs a specimen holder commonly useable in a pre-hydrolysis concentration operation thereby lessening the need to handle specimens in a transfer step and thus eliminating a handling that could expose the specimens to contamination.

An additional object is to provide a hydrolysis unit in which the sample chamber in which the specimens are hydrolyzed is comprised of material inert to the effects of and non-reactive with the hydrolyzing agent and/or the amino acids.

Another object is to provide a hydrolysis unit which embodies a specimen holder capable of holding a substantial number of specimens and which specimen holder is easily inserted in and removed from the unit.

Still another object is to provide a hydrolysis unit which embodies cooling means to facilitate cooling of the specimens as well as the specimen chamber structure on completion of a hydrolyzing cycle thereby shortening the overall hydrolyzing processing and expediting reuse of the unit for subsequent hydrolysis activity.

A further additional object is to provide a hydrolysis unit in which hydrolysis takes place in a sample chamber within a sealable casing so that inability to fulfill an initial requirement for evacuating the casing, signals a unit failure requiring corrective action before hydrolysis can proceed.

A still further object is to provide a hydrolysis unit in which the sample chamber structure is during hydrolysis enclosed in a sealable casing which can be evacuated during hydrolysis so that the space of such casing enclosure can serve as a relief chamber to accommodate pressurized escape flow from the sample chamber in the event there be a failure of sample chamber seal means.

Another object is to provide a hydrolysis unit which embodies a control unit to control the hydrolysis operation, the control unit in turn being powered through an uninterrupted power supply to maintain control unit operation at all times during hydrolyzing so that in event of mainline electrical failure or voltage failure, the control unit can continue functioning to maintain specimen and hydrolysis cycle stage protection during the interruption period.

Briefly stated, there is provided a hydrolysis unit and method by which amino acid-containing specimens are hydrolyzed, the unit including a specimen holder in which a number of specimens can be received. This holder has an upper face side against which a cover can be tightly engaged to seal compartments formed in the holder and define a sample chamber in which the specimens are received and will be hydrolyzed. The holder and cover are housed in a sealable casing, and heating means are provided to apply heat to the specimens while same are in contact with a hydrolyzing agent, this being done while the casing is sealed from the ambient atmosphere and the holder compartments in turn sealed from the casing enclosed space. The unit embodies means optionally to impose vacuum on the casing interior during the hydrolysis cycle, or to fill the casing enclosed space with an inert gas as a cooling expedient following hydrolysis. The sealable nature of the sample chamber and casing interior facilitates pre- and/or post-hydrolysis cleaning and purging of the holder compartments. This not only insures specimen contamination avoidance during hydrolysis, but enables post-hydrolysis removal of residues which in subsequent hydrolysis would represent contamination source. Means are provided to cool down the specimen holder on completion of a hydrolysis cycle to shorten the overall hydrolysis procedure and facilitate further handling of the hydrolyzed specimens as well as early reuse of the unit for further hydrolysis practice.

According to a feature of the invention, there is provided a hydrolysis unit for hydrolyzing amino acid-containing specimens such as proteins, peptides and the like in an operation that involves heating the specimens while same are in contact with a hydrolyzing agent so as to break down specimen amino acids to various discrete ones of such forms of acid present in the specimens, the unit including a specimen holder having an upper face and at least one specimen receiving compartment formed in the face. A cover engages with the specimen holder upper face for sealing the specimen compartment therewith defining a sample chamber. A casing is provided and has a lower casing part in which the specimen holder is removably received. The casing includes an upper casing part, with the cover being carried in this upper casing part. Means are provided for supporting the lower and upper casing parts such that at least one is moveable relative to the other and between a position wherein the one casing part is remote from said other casing part to a second position in which the one casing part is mated to the other and defines therewith a casing enclosure enclosing a space in which the specimen holder and cover are disposed, the cover when the lower and upper casing parts are mated tightly engaging the specimen holder upper face thereby isolating said specimen receiving compartment from the casing enclosure space. Means are provided for introducing heat into a specimen receiving apartment whereby a specimen present therein is heated to hydrolyzing temperature, this means maintaining said compartment heated until a predetermined hydrolysis of the specimens has taken place.

Further features provide means for pre-hydrolysis purging of the sample chamber to remove oxygen presence as well as post hydrolysis cleaning of same, means for cooling the specimens and sample chamber on completion of the hydrolysis cycle, use of polytetrafluoroethylene cover and specimen holder parts to resistant attack thereon by a hydrolyzing agent and amino acids, a slidable mounting of the casing lower part to a position laterally displaced from the upper casing part so that easy access to the lower casing part is provided for insertion/removal of the specimen holder, and a power operated mating of the casing parts to seal the casing and hold it so sealed during the hydrolyzing cycle as well as during post-hydrolyzing cool down. Also uninterrupted power supply is provided for continued operation of a hydrolysis unit microprocessor control unit to sustain certain essential hydrolyzing conditions during a temporary main power line failure to thereby prevent specimen loss and/or contamination.

According to a still further feature of the invention, there is still further provided a method for hydrolyzing amino acid-containing specimens such as proteins, peptides and the like to break down the specimen acids to various discrete ones of such forms of acid present in the specimens, which method involves confining the specimens in a sealed sample chamber and in the presence of a hydrolyzing agent and enclosing the sample chamber in a sealed casing. Vacuum is drawn on the casing chamber to insure that casing chamber and sample chamber seal integrity is present. Following this, a condition of vacuum can be imposed on the sample chamber to therewith withdraw oxygen and any residue from the sample chamber. This vacuum imposition on the sample chamber is then terminated, and an inert gas is flowed into the sample chamber. It is also possible to first fill the sample chamber with inert gas and then draw vacuum on same. The sample chamber is then sealed from the inert gas source following which, the specimens are heated for a predetermined time and at predetermined temperature to hydrolyze the specimens into discrete amino acid forms.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENT

Figure 1:
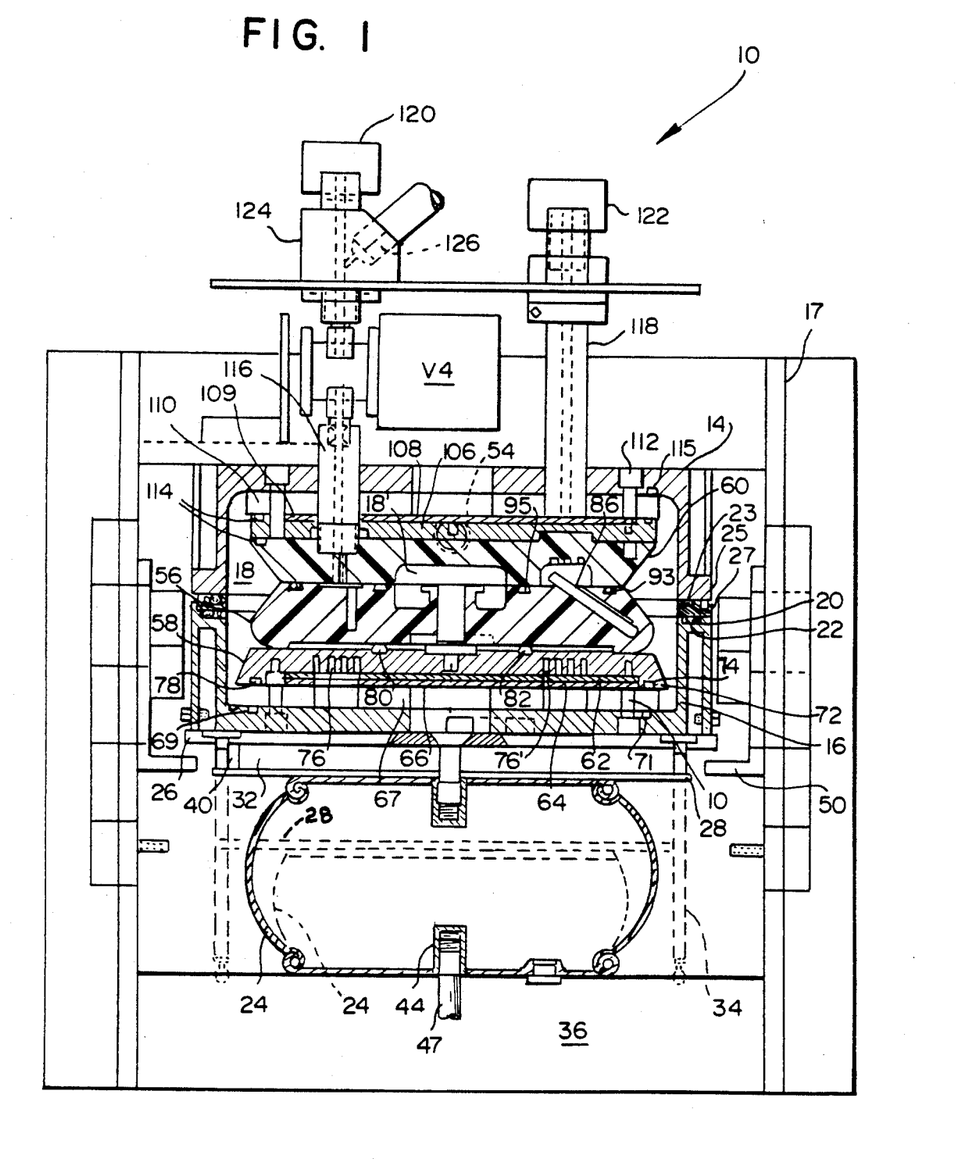
FIG. 1 is a vertical central sectional view of the hydrolysis unit constructed in accordance with the principles of the present invention and showing various constructional features, the casing upper and lower parts being mated and the cover being tightly engaged with the upper face of the specimen holder.

Referring to FIG. 1, the hydrolysis unit 10 is a compact structure conveniently mountable in use position on a laboratory workbench, workstand, movable cart etc. Sources of electricity, a pressurized inert gas and/or compressed air will be available at the use site. Further, a source of vacuum such as a SAVANT Instruments, Inc. vacuum pump Model VP100 or Model VP 190, and a refrigerated trap such as a SAVANT Model RT4104 will be employed with the operation of the unit 10, representative depictions of these last-mentioned devices being shown in FIG. 10.

Figure 2:
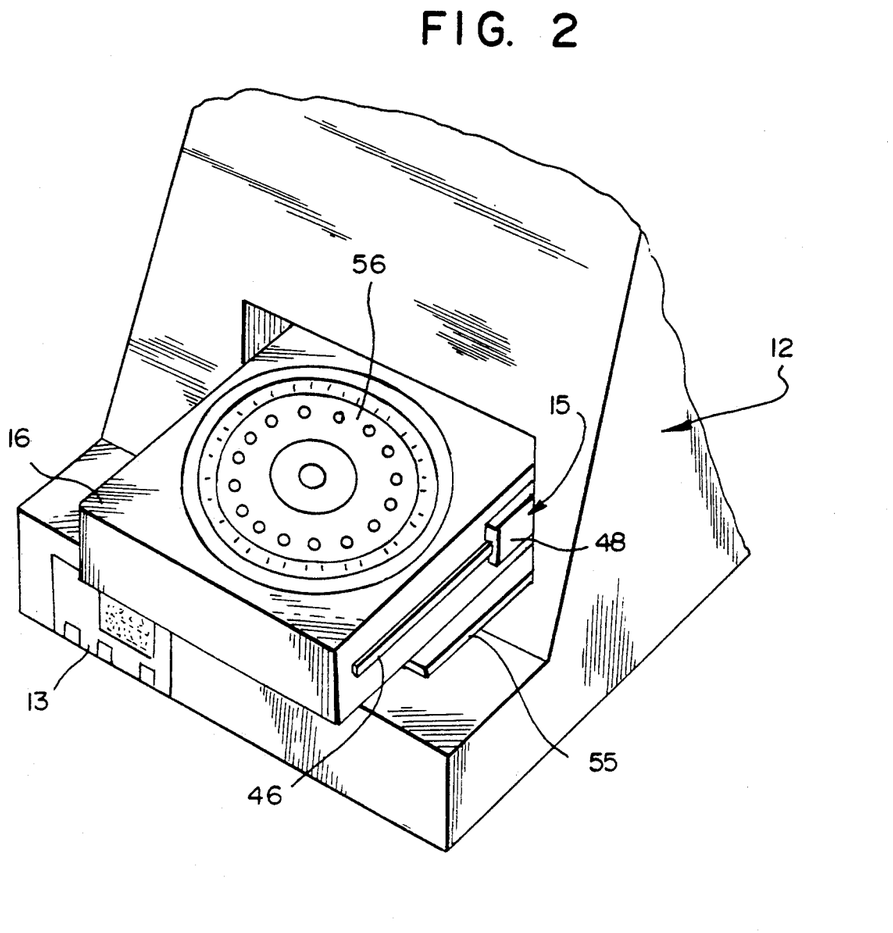
FIG. 2 is a fragmentary perspective view of the front part of the FIG. 1 unit depicting certain aspects of unit construction involved in the sliding mounting of the casing lower part to laterally position it relative to the upper casing part in a clearance positioning that allows simple and ready insertion/removal of the specimen holder from the lower casing part.

With reference again to FIG. 1, the operating components of unit 10 are carried in a housing shown generally at 12 in FIG. 2. This housing 12 is constituted of various housing external panels and internal frame or support structure on which the operating components of the unit are mounted and which will be described in some detail later on. A lower front part of the housing includes space wherein a pull-out assembly 15 locates, the assembly including a later described lower casing part in which is received a specimen holder, this assembly being shown particularly in FIG. 2. Also, the housing will include a microprocessor space section wherein a microprocessor control unit 13 by which unit and hydrolyzing cycle operation can be controlled is housed. Alternatively, this control unit can be a separate component sited close by to unit 10.

Referring again to FIG. 1, unit 10 includes a sealable casing defined by mateable upper and lower casing parts 14, 16, these parts being of, e.g., aluminum, the upper casing part 14 having fixed location in the unit being held with fixing screws, bolts or other such means (not shown) to suitable frame structure 17 in the unit, while the lower casing part 16 can be slid relative to the upper casing part in each of two orthogonally disposed sliding travel paths. The casing parts are shown in mated condition in FIG. 1 in solid lines and enclose chamber space 18, confronting lower and upper faces of the respective parts 14, 16 being in contact during mating and there being encircling seals constituted of a face groove 20 formed in one part and a seal ring 22 received in the groove 20, while a second seal ring 23 is received in groove 25 of an intermediate ring 27 positioned between the casing parts. These seal rings deform under the mating force application of an expandable member 24 in manner as will be given below. Two seal rings of the O-ring type are used to allow for any differential thermal expansion of either part as occurs during hydrolysis thereby insuring that vacuum tight sealing of the casing parts is effected when the casing is closed. Intermediate ring 27 is as noted, employed in connection with this mating. the ring 27 having limited axial captive movement capability, being joined captively to either one of the two casing parts.

Lower casing part 16 sits loosely on a plate 26 which plate in turn is fixed to a another plate 28 as by means of fixing screw (not shown), the two plates being intervened by a ceramic insulator plate 32. Plate 28 is a radiator plate provided to effect radiation of heat away from the structure of expandable member 24 to protect same from the heat generated during the hydrolysis cycle. Plate 26 has a number of tension coil springs 34 attached thereto at one spring end with the other spring ends being fixed to a unit base frame part 36, plate 28 having suitable openings therein for spring pass through and plate 32 being provided with spring clearance notches as at 40.

Figure 10:
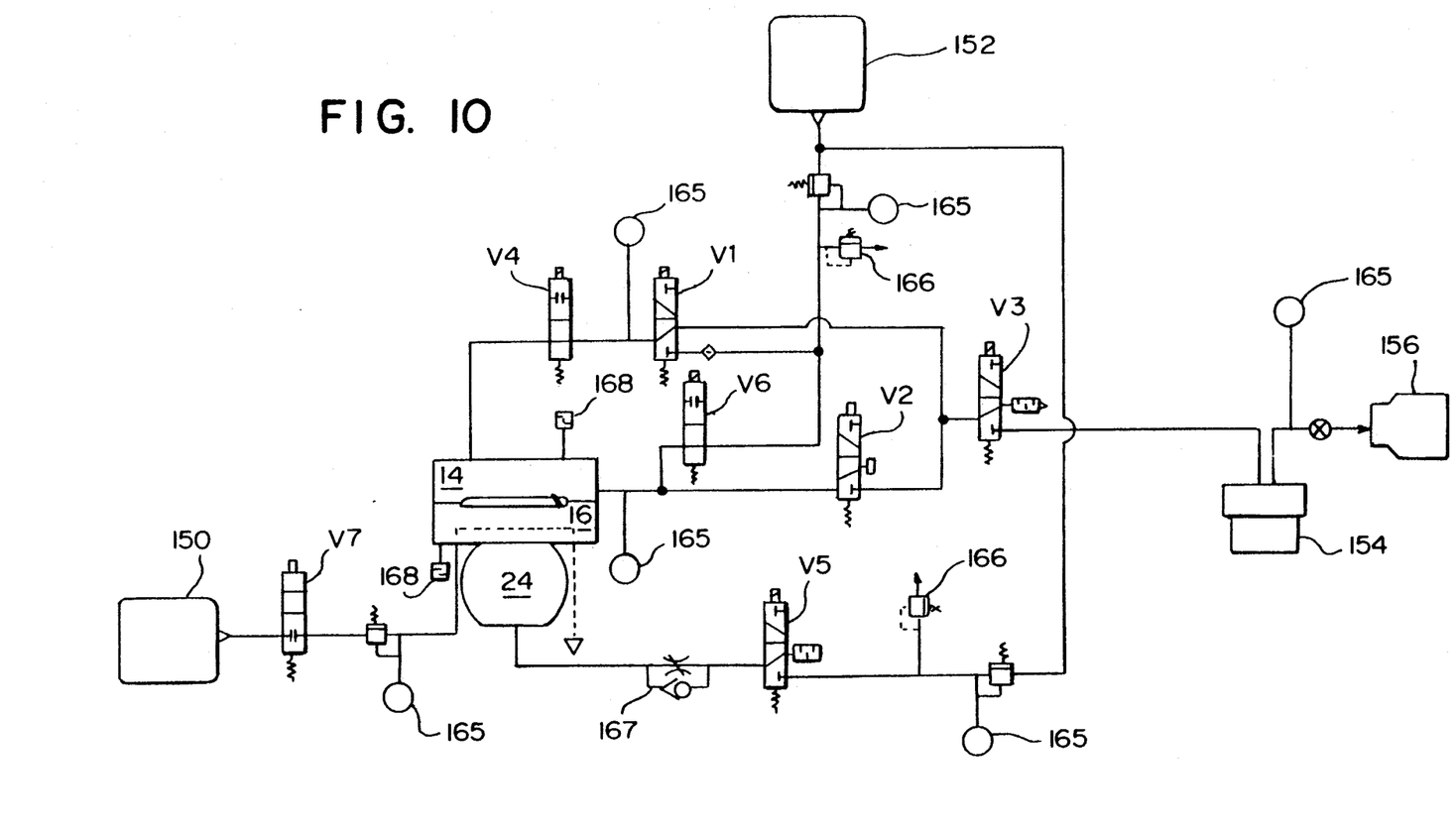
FIG. 10 is a flow diagram depicting the several piping and valving components embodied in the hydrolysis unit.

Expandable member 24 is an inflatable bladder disposed at the underside of plate 28 and sits on frame part 36, a fitting 44 being provided on the bladder for receiving hose piece 47 which in turn connects with a source of pressurized gas (as depicted in FIG. 10) by which the bladder is inflated to the full line position shown in FIG. 1. When no pressure is present in the bladder, it relaxes under the impetus of pressure of springs 34, to the position shown in dashed lines in FIG. 1 and the assembly of plates 26, 28, 32 correspondingly lowers some distance which results in the lower casing part 16 moving away vertically downward from its mating position with the upper casing part, this result following because of the bias action of springs 34, the springs being shown in FIG. 1 in their stretched or tensed condition having been so tensed by the much greater magnitude of force exerted by the bladder when it is inflated. It is seen that in this mode of movement, lower casing part 16 moves in straightline, generally vertically oriented travel between its lowered remote from the upper casing part position, to an elevated position wherein it tightly mates with the upper casing part 14.

The lower casing part 16 also has a second, generally straightline travel path in which it can move from its position remote from the upper casing part to one in which it is laterally displaced from that remote position, the travel path in this instance being generally horizontally disposed and orthogonal to the first-described travel path. This capacity to slide the lower casing part 16 in lateral movement allows positioning thereof wherein unencumbered access to the lower casing part is possible for insertion and removal of a specimen holder in and from the lower casing part.

Figure 9:
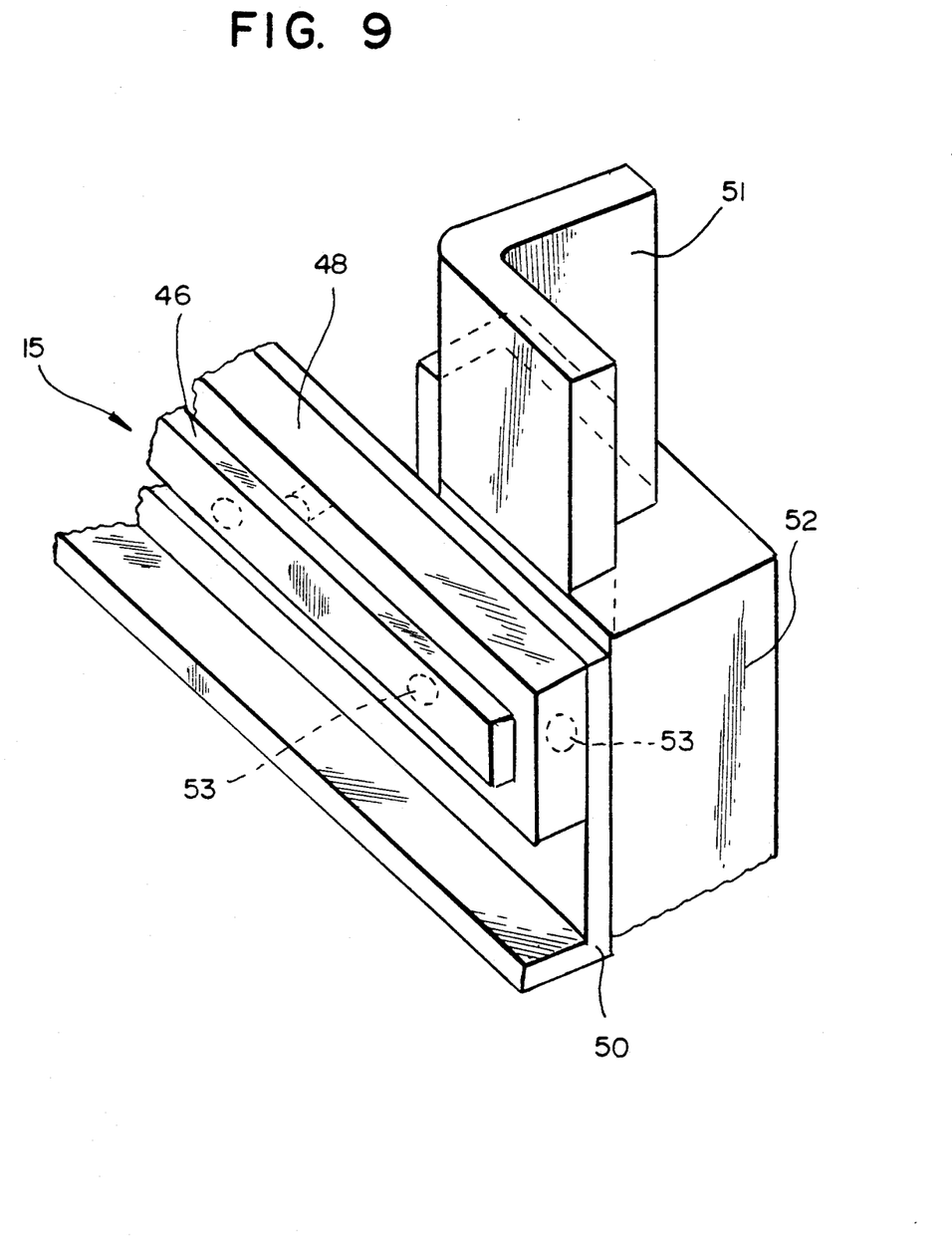
FIG. 9 is a fragmentary perspective view of one manner of structure which can be used for supporting the lower casing part for sliding movement in each of two orthogonally disposed sliding travel paths.

This second travel path movement is effected by securing the lower casing part at each of opposite sides thereof to one of a pair of telescoping arms 46, 48 of ball or roller pull out assembly 15, a pair of such arms being at each of the opposite sides. FIG. 9 illustrates the structure by which this is accomplished. A fixed frame member 51 in the unit provides an anchor to which vertically slidable carriers 52 are connected, these carriers having angle brackets 50 fixed thereto. The arms 48 in turn are slidably fixed to the brackets 50. Both arms 46 and 48 can move on friction reducing mountings 53, which mountings can be rollers or they may be balls, and arm 46 can slide on arm 48 and arm 48 slide on the brackets. FIG. 2 illustrates the lateral positioning of the lower casing part 16 and it is readily noted therefrom that front access clearance space is amply provided for inserting and removing a specimen holder.

Further in connection with this arrangement and as will be seen from reference to FIG. 2, proper retraction of the lower casing part as an essential step to further hydrolysis procedure is necessary to allow the unit to proceed in operation. Door 55 which is opened to pull out the lower casing part must be closed to allow energizing of the expandable member 24, since safety and cut-out control is incorporated in the unit that will prevent pressurization of the expandable member unless the door is closed—this prevents possible worker hand injury from the elevation of the casing as it cannot be elevated with the door open.

The upper casing part 14 is at its rear side as shown in FIGS. 1 and 10, provided as at 54 with a fitting 54 where connection is made with piping or a hose leading to a source of vacuum or inert gas as will be detailed further in this description.

The casing constitutes structure in which is situated a separate specimen chamber structure and which specimen chamber structure is comprised of, among other things a specimen holder 56, a saddle plate 58 on which the specimen holder sits, a cover 60 that is used to seal the specimen holder, and other components including heaters, all of which will be described below and with reference being made in the ensuing description to FIGS. 1 and 3-8 which detail the construction and make apparent the function of these components.

Saddle plate 58 is a metallic generally circular plan outline member and sits on top of the successive downwardly placed elements of an aluminum heat sink disc 62, a high-resistance membrane type electric heater 64, another aluminum plate 66, and a ceramic plate 67 set on the inner horizontal face of the lower casing part, there being an encircling course seal 69 set in groove 71 formed in the said casing lower part inner horizontal face. These elements are held tightly assembled with screw means 70, and it will be noted that the saddle plate is peripherally skirted as at 72 so that the disc 62, heater 64 and aluminum plate 66 are encircled by the skirt. The underface of peripheral skirt also is grooved as at 74 for reception of a seal member 78. It also will be seen that a number of inlet grooves 76 and outlet grooves 76' exist at the underside of the saddle plate and traverse an encircling course therein, such grooves being in communication with openings in the disc 62, plate 66, heater 64 and plate 67 which openings in turn can be placed in communication with a source of cooling gas at the end of a hydrolysis cycle which will be referred to again later in connection with description of FIG. 12.

When specimen holder 56 is inserted in the casing lower part 16 it sits on a cushioning ring 80 of elastomeric material disposed in a saddle plate upper face groove 82. This ring is split, being in reality two semicircular parts and arranged that confronting edges of the two parts define a flow through point for a pressure equalization path between chamber space 18 and interior space 18' which exists at the underface of the specimen holder 56. Specimen holder 56 is a disc-like member of circular plan outline and is made of a 25% glass filed polytetraflouroethylene (PTFE) composition. Use of PTFE insures that the normally corrosive hydrolyzing agent and/or amino acid which contacts the holder and later-described cover, does not produce any adverse effect to these components.

Figure 5:
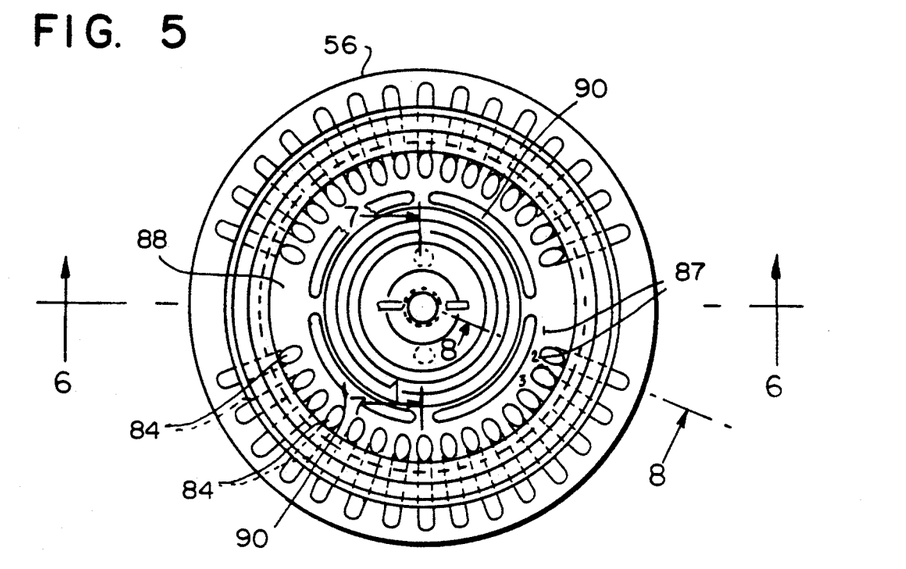
FIG. 5 is a top plan view of the specimen holder.
Figure 6:
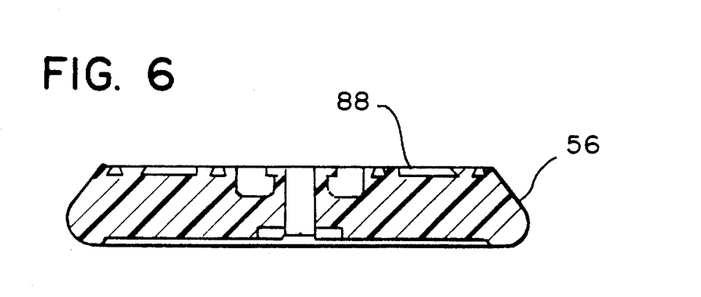
FIG. 6 is a sectional view taken on the line 6—6 in FIG. 5.
Figure 7:
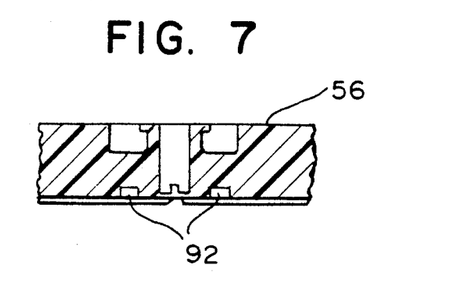
FIGS. 7 and 8 are sectional views taken on the respective lines 7—7 and 8—8 in FIG. 5.
Figure 8:
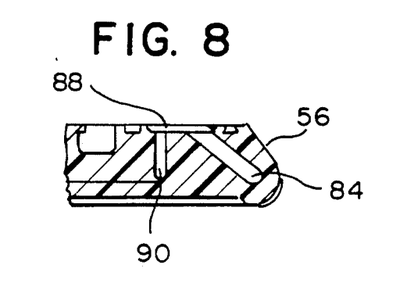

The specimen holder is as can be seen especially in FIGS. 5 and 7, provided with an array of inclined, radially outwardly directed blind bores 84 arranged in two groupings of bores one on each side of the diameter of the holder, these bores each being receptive of a specimen-containing vial or tube 86, one of which is shown in FIG. 1. The respective bores can be provided with indicia markings 87 adjacent each one as a means for identifying specimens used during the hydrolysis. The bores initiate at an encircling depressed groove 88 formed at the top face of the holder and hence are in communication with this groove. The outer radial margin of groove 88 is inclined inwardly at an angle of about 35 degrees, this angulation being effective to prevent spill of agent and/or specimen present in the groove when the specimens are subjected to a concentration operation in the holder. Spaced radially inwardly from the blind bores are a number of reservoir passages 90, these passages being blind at their end and spanning each approximately a quadrant extent in the holder, but the reservoirs having ready communication with groove 88 and adjacent or near ones of the bores, the reservoirs serving to hold hydrolyzing agent during the hydrolysis cycle.

The bores 84 it is seen extend inclined outwardly from top to bottom in the holder in manner that correspondingly orients the tubes 86 received therein. By giving this orientation to the bores, the specimen holder can be the same rotor device used for holding specimens during a pre-hydrolyzing concentration operation such as can be practiced with a SAVANT SPEEDVAC concentrator. In this way a transfer operation of specimens from one to another holder for hydrolysis is eliminated and avoidance of possible contamination producing activity achieved. This dual use character of the specimen holder requires the underside of the holder have two reciprocally disposed locator openings 92 as shown in FIG. 7 to engage with an upwardly formed projection on the saddle plate (not shown) to properly circularly position the specimen holder to align with certain flow passages in the cover 60 and elsewhere as will be seen later.

The specimen holder carries two encircling O-rings, one such ring 93 being adjacent the periphery of the holder and the other ring 95 being spaced inwardly radially some distance adjacent to but inwardly of the reservoir passages 90. When the lower face of the cover 60 is engaged with the upper face of the holder, the space between the O-rings defines the sample chamber in which hydrolysis occurs, and this sample chamber is isolated by the O-rings from the casing chamber space 18 and its interior space part 18'.

Figure 3:
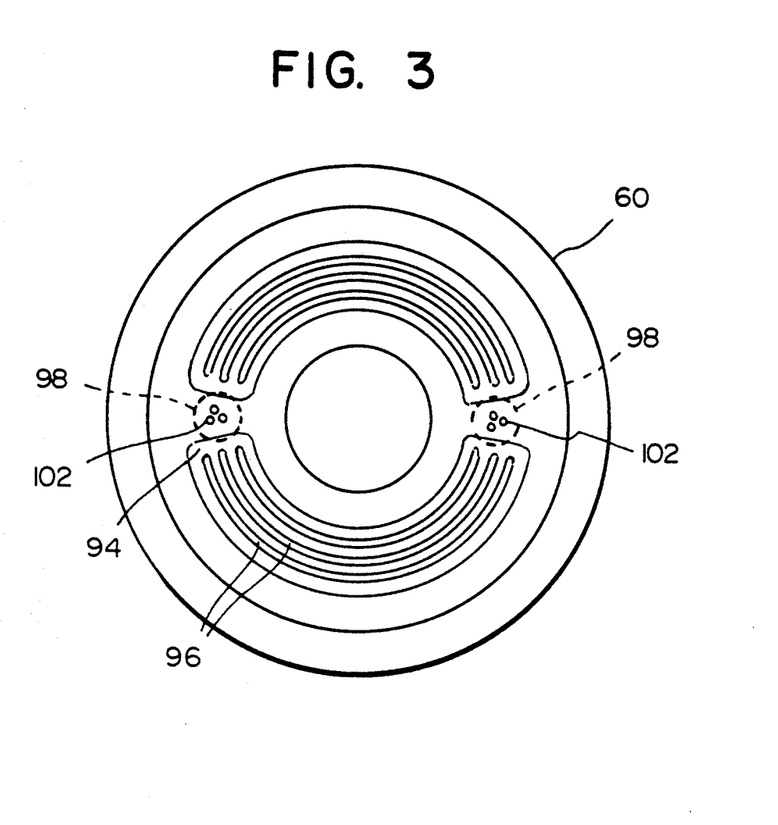
FIG. 3 is a plan view looking at the bottom face of the cover which tightly fits the upper face of the specimen holder when the casing parts are mated.
Figure 4:
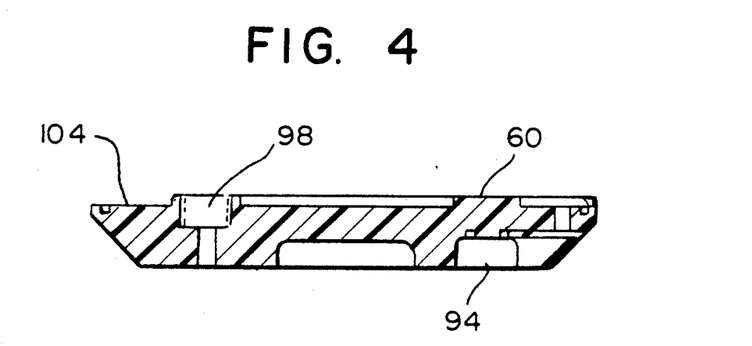
FIG. 4 is a diametrical sectional view of the cover when it is normal upright use positioning.

With reference to FIGS. 3 and 4, cover 60 also is a circular plan profile disc-like component and is made of the same material composition as the specimen holder. As noted on FIG. 3, the lower surface of the cover is configured with enlarged slots 94 disposed symmetrically on opposite sides of a diameter of the cover, these slots as seen in FIG. 4 extending upwardly some distance from the cover lower face and in each case being surmounted by a number of spaced but following course crown slots 96. A pair of reciprocally located bores 98 extend downwardly a distance from the top surface of the cover and then terminate in favor of a group of smaller bores 102 that pass to the cover lower surface. The purpose of these bores will be made clear from later given description.

The cover upper surface is stepped at a marginal area thereon as at 104, and this step functions in respect of interlocking joinder of the cover 60 with other components now described. As seen in FIG. 1, an aluminum heat sink plate 106 lies interlocked on top of the cover, and a high resistance type membrane heater 108 overlays the plate 106 and in turn is topped by another metal plate 109 which itself is topped with a ceramic plate 110. These foregoing elements arranged in sandwiched relationship, are fixed to the upper casing part 14 with fixing screws 112.

Seals 114 are provided in the above sandwiched assembly and a seal 115 seals the sandwiched assembly where ceramic plate 110 contacts the underface of the upper casing part 14. Thus it is noted that in closing the casing, the specimen holder is elevated upwardly tightly against the fixedly positioned lower surface of the cover, and when the casing is closed with its parts mated, its interior casing chamber space 18 is isolated from the outside ambient environment, and the sample chamber constituted of the sample-containing tube bores 84, depressed groove 88, reservoir passages 90 and the cover slots 94 is in turn isolated from the casing chamber, this last-mentioned isolation being effected with seals 93, 95 previously described.

Again referring to FIG. 1, a pair of PTFE pipes 116, 118 are provided for the unit and communicate at lower ends of each with the bores 98 formed in cover 60, the upper ends of the pipes being capped with readily removable capping members 120, 122, these pipes being used in conjunction with sample chamber purging and component cleaning. Pipe 116 has an upper fitting 124 in Y-Branch form to permit joinder of a hose thereto at 126 for connecting the vacuum pump to the sample chamber as will be described later. Further a sample chamber control valve V4 is in the pipe 116 for controlling flow through or blocking of flow in pipe 116.

Completion of a hydrolyzing cycle finds the sample chamber and casing quite hot and for that reason end-of-cycle cooling can be employed and which will be described in more detail below regarding the operation of the unit for hydrolyzing specimens. It is noted here though that cooling of the interior of the casing chamber can be effected with compressed gas flow into that chamber. It is also desirable that external casing cooling be carried out. This will be done, for example, with fan cooling and employing the cooling means shown in FIG. 11. With reference to that FIGURE, a pair of cooling fans 130,132 are mounted in the unit at opposite sides of the casing. They are positioned to flow cooling streams of ambient air against the casing to cool it. This cooling effect supplements other cooling procedure as will be described so that early access to the unit for specimen removal is possible and additionally, worker safety in handling steps thereafter is insured.

Description now will be given of hydrolyzing amino acid-containing specimens. The specimens are placed in sample tubes and the tubes in turn inserted in the inclined bores 84 of a specimen holder 86. The specimen holder is then inserted in a concentrator and the specimens concentrated. The specimen holder and sample tubes will of course have been prior cleaned to avoid contamination possibility. The specimen holder is then removed from the concentrator and is ready for placement in hydrolysis unit 10. Preliminarily, the unit lower casing part has been moved out to lateral position.

Before placement of the specimen holder in the unit 10, hydrolyzing agent such as hydrochloric acid will be placed in the reservoirs of the specimen holder if vapor hydrolysis is to be practiced, or if liquid hydrolysis is to be practiced, the agent will be pipetted directly onto the top of the specimens in the tubes, and also some agent will be placed in the reservoirs.

Prior to loading the holder in the casing part 16, door 55 at the front of the unit is opened and the lower casing part is slid out to its lateral position. The specimen holder is then placed in the lower casing part, being hand rotated as required to receive a locator pin in one of the locator openings at the bottom of the specimen holder to properly orient the holder. This also assures that when the cover is closed against the holder no misalignment placement of the holder exists, since if such was present, the cover could crush the specimen tubes. With this done, the lower casing part is slid back to its position remote below but in alignment with the upper casing part and door 55 is closed. Pressurized gas is then supplied to the bladder 24 to expand it against the bias of springs 34, and the lower casing part 16 will be moved up into tight sealed, mating contact with the upper casing part 14. Incident this closing of the casing, the specimen holder 56 also elevates into sealed contact with the cover 60 thereby creating a sealed sample chamber in which the specimens are located. Microprocessor control unit 13 is programmed to control the ensuing hydrolysis operation steps.

As a first matter, the casing chamber 18, 18' will be connected to vacuum and evacuated. This will be done for a number of reasons, One, it serves to indicate that the casing is properly closed, that the specimen holder is in place and properly oriented, and third, that the requisite seals are holding. If vacuum cannot be draw down to the required level, the procedure must be aborted and the cause of non or poor vacuum draw in the casing found and corrected. If the vacuum holds as intended, the hydrolysis procedure will continue. First, the sample chamber is purged to remove oxygen presence. This can be done by controlling the valves shown in FIG. 10 to, for example, admit nitrogen from a source to the sample chamber followed by imposing a vacuum on the sample chamber to draw out any air therein which has been displaced by the nitrogen. This purging can be effected in repeated steps of vacuum draw of, for example, 10 vacuum purges of short duration.

Hydrolysis now can proceed under the control of control unit 13. Hydrolysis temperature and time of hydrolysis will have been preset in the control unit. Time of hydrolysis can depending on sample type etc, vary from minutes to hours. Actual times in each instance will follow user pre-established protocols. Temperature will vary also in accordance with specimen type etc, but generally will be one in a range about 100 degrees C. to about 175 degrees C. During hydrolysis and where demand for heating is defined, both of heaters 64, 108 will be operated responsive to the temperature of the sample chamber component with which it is associated. Thus heater 64 will operate with regard to maintaining a predetermined temperature in the specimen holder and sandwich assembly of elements therebelow, and heater 108 will operate responsive to temperature condition in the cover 60 and the sandwich assembly thereabove. With application of heat to the specimens, hydrolysis proceeds until the end of the preset cycle time of hydrolysis.

During hydrolysis, pressure will build up in the sample chamber to a value of between about 15 to about 90 p.s.i. Since this order of pressure is present, and if the sample chamber leaked, there could in prior procedures using prior hydrolysis equipment be presented serious hazard to workers. However, with unit 10, the enclosure of the sample chamber within a sealed casing, as well as the evacuation of the casing chamber provide against such a happening presenting danger to a worker near the unit. The vacuum in chamber 18, buffers or mitigates the effect of any high pressure fluid entry to such chamber and reduces chance that such fluid could pass through the casing seals. Further as FIG. 10 shows, unit monitoring is extensive so that a hazardous leak is immediately detected and the unit can responsively be shut down. Further it is to be noted leak occurrence at the outset of a cycle also can be used to signal the unit should not and will not be further operated until the leak cause is found and corrected.

Figure 12:
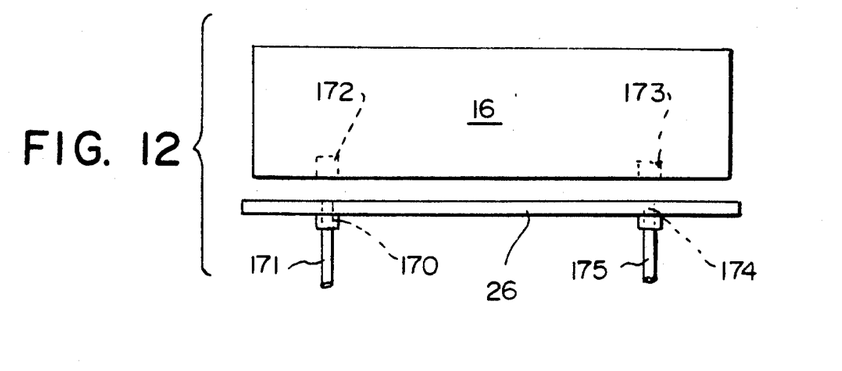
FIG. 12 is a fragmentary elevational view taken from the rear of the unit an depicting an arrangement with which cooling gas can be flowed into the lower casing part during a cooling operation at the end of a hydrolyzing cycle.

Before removing the specimens from the unit, it is desirable to effect cooling to bring the samples and the specimen holder itself down to a user handling temperature, e.g., a temperature of about 60 degrees C. or lower. Cooling can be accomplished in a number of ways. For example a cooling stream flow of compressed air or of an inert gas can be passed into the casing chamber 18 exterior of the sample chamber components to cool same. Additionally and as seen from FIG. 12 compressed air can be introduced at the underside of the lower casing part 16. FIG. 12 shows the casing part 16 and plate 26 spaced apart as same are when the casing part is in lowered position. However during hydrolysis, the plate 26 is urged against the casing part and in that position, an inlet opening 170 in the plate with supply hose 171 aligns in communication with port 172 that communicates cooling air flow to grooves 76 at the underside of the saddle plate. Outflow is through port 173 via plate outlet opening 174 and outlet hose 175.

Figure 11:
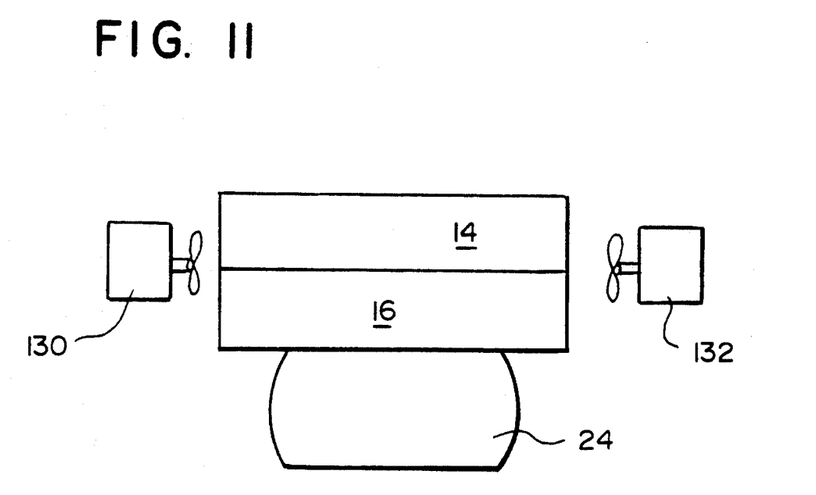
FIG. 11 is a diagrammatic depiction of the unit looking from the front to rear and illustrating mounting of cooling fans adjacent the casing, certain other parts of the unit being omitted for sake of clarity in depicting the cooling fans.

Also as earlier noted with reference to FIG. 11, external casing cooling also can be accomplished. When the requisite sample temperature is reached, the casing lower part can be dropped from mating with the upper part and slid to lateral position thereof. The specimen holder is then removed and further sample handling in respect of the required follow-up derivatization, separation and measurement is pursued. Any one, a combination or all of these cooling practices can be followed at the same time.

An important feature of the invention is the ease and certainty with which the sample chamber structure can following a hydrolysis operation be cleaned. In carrying out such a cleaning, pipes 116, 118 will be used. First, the casing will be sealed with an empty specimen holder set in place and the casing will be evacuated to be sure a vacuum can be held, this being necessary to insure a leak is not in the sample chamber components because in a subsequent cleaning operation, cleaning agents and hydrolysis residue could be passed through the leak to the casing interior which is an event to be prohibited. Optionally, a cleaning rotor can have been inserted in the casing in place of the specimen holder, this cleaning rotor having a smoother upper face than the holder 56. A cleaning agent such as methanol, a mixture of water and methanol or other suitable agent can then be poured into pipe 116 (cap 120 removed). The cleaning agent will flow into the chamber and back up through pipe 118 (cap 122 removed)—the sample chamber valve V4 being open during this cleaning. After desired agent quantity has been flowed through the sample chamber, pipe 116 is capped and pressurized inert gas is admitted via pipe 116 to expel or blow out the agent remaining through pipe 118. This cleaning can repeated a number of times if desired. HPLC-purity water also may be employed in the leaning as either a cleaning and/or flushing agent.

Drying of the sample chamber can be thereafter effected by connecting the sample chamber with the vacuum pump to withdraw any cleaning agent residue therefrom, such withdrawn residue collecting in the condensate trap. Additionally, drying heat can generated by operating the heaters for such purpose.

An important feature and advantage of the unit 10 is embodiment therewith of means to maintain certain hydrolyzing operation conditions during the hydrolyzing cycle in the event of an electrical power failure or momentary voltage interruption that otherwise would erase the program in the microprocessor and hence terminate the cycle. Premature cycle termination could result in specimen loss or erroneous result if hydrolyzing is renewed with a specimen after elimination of the power failure. Such means will be described next.

Figure 13:
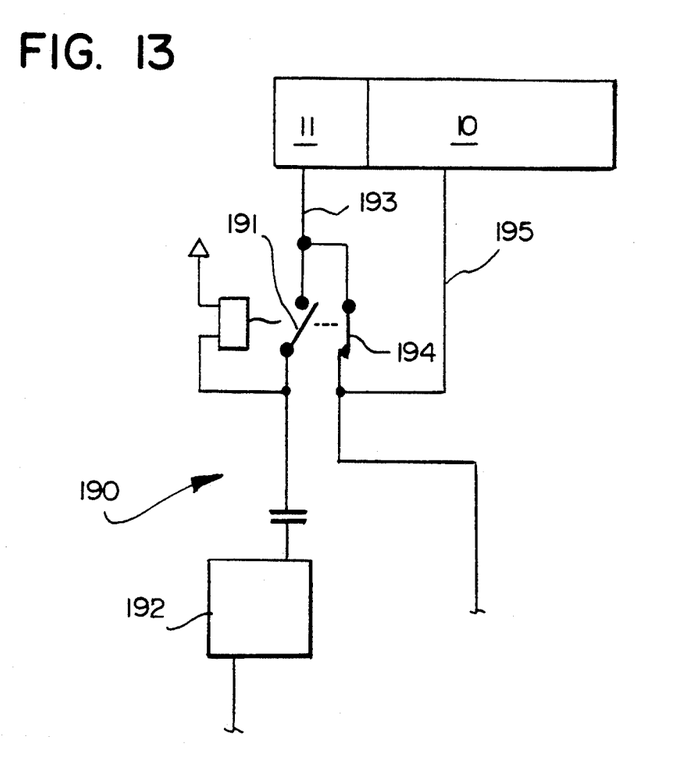
FIG. 13 is a wiring schematic of the uninterrupted power supply device employed for powering the hydrolysis unit control unit to insure holding of essential hydrolyzing conditions during a hydrolyzing cycle in the event of power failure or line voltage interruption thereby eliminating potential for loss of the specimen.

Referring to FIG. 13, an uninterrupted power supply means is shown generally at 190. This includes a self-latching contact 191, a power supply module 192 and a power leg 193 connecting contact 191 to control unit 11. Line voltage supply to control unit 11 is via closed contact set 194 and line voltage supply to the non-microprocessor electrical components of unit 10 is by way of power leg 195. When supply module 192 is plugged into the circuit, self-latching contact 191 will close and contact 194 will be opened. All power to the control unit then will supply through the module so that if a main electrical power failure occurs or line voltage through power leg 195 is interrupted, it will have no effect on the operation of the control unit which will continue on the power supplied from the built-in power source in the module 192 which assumes such function without affect on the microprocessor.

While certain electrical components in unit 10 will on power failure, be unable to function or will become passive, control unit 11 will continue to supply such power function as is required to insure that the main sample chamber valve remains closed to thereby maintain the sample chamber isolated. Further, power supply will continue to the valve controlling admission of pressurized gas to the expandable member 24 so this member maintains lower casing part 16 urged up tightly in mating contact with the upper casing part 14 and thus chamber 18 tightly sealed from the outside atmosphere.

It is seen that where a power failure takes place, a specimen hydrolyzing cycle need not be aborted. Since most power failures are only momentary or of otherwise short duration, the continuance of the sealing of the sample chamber and the vacuum chamber for the short times involved as well as continuance of control unit function and the particular hydrolyzing cycle inputs therein present, allows resumption of hydrolyzing immediately upon restoration of main power supply. The uninterrupted power supply means can include independent power source therein which will function for a time figured to span almost all main power failure periods anticipated will occur. For example, the power supply can be such as to last for one, two or more hours before becoming depleted and hence incapable of sustaining control unit operation.

The operation of the hydrolysis unit involves employment of the piping, valve and other devices depicted in FIG. 10. It will be understood that the various piping, hose, valve and like elements are readily mountable in the housing 12 at suitable locations. For example, most of the valves and gages can be carried at the rear of the unit for convenience of both installation ease as well as maintenance. Also it is understood that operation of these components is controlled by control unit 13.

Referring now to FIG. 10, compressed air source 150, pressurized nitrogen gas source 152, refrigerated condensate trap 154 and vacuum pump 156 are items not embodied in the unit but are necessary and will be present adjacent therewith as will be a source of mainline electrical power supply. Also the arrangement includes a flow control valve 167, pressure and/or vacuum gages 165, relief valves 166 and temperature sensors 168. Elements 165 and 168 it is understood are integrated in the control unit programming as part of the continuous monitoring arrangement utilized in the hydrolyzing procedure and used in carrying out a preset hydrolysis cycle.

Compressed air from source 150 is admitted as required for cooling of the casing by opening valve V7. Pressurized nitrogen for inflating expandable member will flow from source 152 into the member when valve V5 is opened, this valve communicating with atmosphere normally. Similarly, the main vacuum valve V3 connected with the piping leading to trap 154 and vacuum pump 156 will normally connect to atmosphere, but will shift to connect the pump with the piping legs leading to the casing when it is to be evacuated. When vacuum is to be drawn on the casing, valve V2 also will be opened and it will be noted valve V6 connected to the nitrogen source will be closed. Conversely if nitrogen is to be flowed into the casing for cooling purposes, the orientation of the last two valves will be reversed.

Valve V4 will be opened whenever either vacuum draw or nitrogen inflow is to take place in the sample chamber and valve V1 will be oriented in correspondence to the particular one of such events as is taking place. In other words shifting of valve V1 to one or the other position, establishes connection to vacuum source or the pressurized nitrogen source.

As was pointed out earlier, uninterrupted power supply can be embodied in the unit to insure that in event of a mainline power failure, normally open valve V4 is powered to close it to thereby assure maintenance of sealing of the sample chamber from outside environments. Similarly, the uninterrupted power supply will maintain power to valve V5 to keep it shifted in the position wherein it connects the nitrogen source 152 with the expandable member 24.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. Hydrolysis unit for hydrolyzing amino acid-containing specimens in an operation that involves heating the specimens while same are in contact with a hydrolyzing agent so as to break down the specimens into their amino acid components, said hydrolysis unit comprising:
   a specimen holder having an upper face and at least one specimen receiving compartment formed in said upper face,
   a cover engageable with said specimen holder upper face for sealing the at least one specimen receiving compartment and therewith defining a sample chamber,
   a lower casing part, said specimen holder being removably receivable in said lower casing part,
   an upper casing part, said cover being carried in said upper casing part,
   means including a frame for supporting said lower and upper casing parts such that one of said upper and said lower casing parts is mounted fixed to said frame and the other casing part is movably mounted on said frame so that it can move relative to the fixed casing part between a position wherein the movably mounted casing part is remote from the fixed casing part to a second position in which the movably mounted casing part is mated to the fixed casing part and defines therewith a casing enclosing a vacuum-tight sealed space in which said specimen holder and cover are disposed, said cover when said lower and upper casing parts are mated tightly engaging the specimen holder upper face thereby isolating said at least one specimen receiving compartment from the casing enclosed space, and
   means for introducing heat into said at least one specimen receiving compartment whereby a specimen present therein is heated to hydrolyzing temperature, said means maintaining said at least specimen receiving compartment heated until a predetermined hydrolysis of the specimens has taken place.

2. The hydrolysis unit of claim 1 in which the said movably mounted casing part is movably mounted on said frame such as to move in a vertical sliding travel path from said position remote from the fixed casing part to the position wherein it mates therewith.

3. The hydrolysis unit of claim 2 in which said movably mounted casing part is movably mounted on said frame such as to be movable additionally in a second sliding travel path from position in which it is remote from the fixed casing part to a second sliding travel path opposite position wherein said movably mounted casing part occupies a position laterally displaced with respect to the fixed casing part whereby said movably mounted casing part is readily accessible for insertion and removal placement of the specimen holder in or out of said movably mounted casing part.

4. The hydrolysis unit of claim 3 in which the second sliding travel path is a horizontal sliding travel path.

5. The hydrolysis unit of claim 4 further comprising power means for moving said movably mounted casing part from position remote from said fixed casing part to the position wherein it mates therewith.

6. The hydrolysis unit of claim 5 in which said power means includes an expandable member connected to said movably mounted casing part, said expandable member normally being in relaxed state but expanding on introduction of a pressurized fluid flow thereto and therewith urging said movably mounted casing part from its position remote from said fixed casing part into mating contact with said fixed casing part.

7. The hydrolysis unit of claim 6 further comprising bias means connected to said movably mounted casing part and acting to normally maintain said movably mounted casing part in its position remote from said fixed casing part, said expandable member when pressurized overcoming bias constraint of said bias means but said bias means returning said movably mounted casing part to said remote position thereof when pressurized fluid flow to said expandable member is terminated.

8. The hydrolysis unit of claim 7 in which said bias means comprises tension springs.

9. The hydrolysis unit of claim 4 in which said movably mounted casing part comprises the lower casing part.

10. The hydrolysis unit of claim 9 in which said frame includes spaced apart frame upright members, said lower casing part including projecting structure at each of a pair of opposite lower casing part sides, said projecting structure being connected with sliding travel path guide means in said spaced apart frame upright members for guiding the vertical sliding travel of said lower casing part when it moves between its said position remote from the upper casing part and its said position of mating contact therewith.

11. The hydrolysis unit of claim 10 in which the spaced apart frame upright members include horizontally oriented and slidable arms carried on said spaced apart frame members, said upright slidable arms being connected with said lower casing part whereby said lower casing part can be slid between its position remote with said upper casing part and said laterally displaced position.

12. The hydrolysis unit of claim 11 in which the upper and lower casing parts have respective lower and upper confronting faces, at least one of said lower and upper confronting faces carrying seal means which when the said upper and lower casing parts are mated deform to tightly seal the casing enclosed space to prevent any fluid flow to or from said casing enclosed space via the surfaces where said upper and lower casing parts are in mating contact.

13. The hydrolysis unit of claim 1 in which at least one of the specimen holder upper face and a confronting face of said cover include seal means carried thereat and which deform to tightly seal the at least one specimen receiving compartment from the casing enclosed space.

14. The hydrolysis unit of claim 1 in which said specimen holder is a disc shaped member, the at least one specimen receiving compartment comprising a bore formed in the disc-shaped member there being a plurality of such bores formed in the disc-shaped member and arranged in a circularly arrayed disposition, each bore being receptive of a specimen-containing open-topped tube member.

15. The hydrolysis unit of claim 14 in which said plurality of bores are blind and dispose inclined from a bore opening at the disc-shaped member upper face outwardly radially and in a direction away from said disc-shaped member upper face.

16. The hydrolysis unit of claim 15 in which said cover comprises a disc of generally coextensive plan outline with that of said specimen holder so that when said upper and lower casing parts are mated, said disc tightly superposes with said specimen holder, said disc having a lower face, there being blind groove means formed in said disc upwardly of its lower face which overlie the plurality of bores of said disc-shaped member and constitute space for receiving vapors evolved from the specimens during heating of same.

17. The hydrolysis unit of claim 1 in which the means for introducing heat comprises at least one heater in thermally conductive contact with at least one of said cover and said specimen holder.

18. The hydrolysis unit of claim 17 in which said at least one heater is in thermally conductive contact with said cover, there being a heat transfer member of high thermal conductivity disposed intermediate said cover and said at least one heater.

19. The hydrolysis unit of claim 18 in which said heat transfer member is aluminum.

20. The hydrolysis unit of claim 19 in which said at least one heater is a high-resistance, membrane type at least one heater, said heater being sandwiched between a pair of aluminum members.

21. The hydrolysis unit of claim 19 further comprising another heater in thermally conductive contact with said specimen holder.

22. The hydrolysis unit of claim 21 in which said other heater is a high-resistance membrane type heater, said other heater being sandwiched between a pair of aluminum members.

23. The hydrolysis unit of claim 1 comprising a source of vacuum and means carried in one of said upper and lower casing parts for connecting said casing enclosed space to the source of vacuum whereby a condition of vacuum can be imposed on the casing enclosed space when said upper and lower casing parts are mated.

24. The hydrolysis unit of claim 23 in which said vacuum connecting means is carried on said upper casing part.

25. The hydrolysis unit of claim 23 in which said source of vacuum is a vacuum pump.

26. The hydrolysis unit of claim 25 further comprising a condensate trap intervening said vacuum pump and said casing enclosed space for condensing and collecting any vapors drawn outwardly from the casing enclosed space.

27. The hydrolysis unit of claim 26 in which said condensate trap is a refrigerated trap.

28. The hydrolysis unit of claim 1 comprising means effective when said cover is tightly engaging the specimen holder upper face for connecting said sample chamber selectively with one of a source of vacuum and a source of pressurized fluid.

29. The hydrolysis unit of claim 1 in which said specimen holder and said cover are made of a material inert to the hydrolyzing agent and to amino acids.

30. The hydrolysis unit of claim 29 in which said material is polytetrafluroethylene.

31. The hydrolysis unit of claim 1 further comprising means for cooling said casing enclosed space upon completion of a specimen hydrolyzing cycle.

32. The hydrolysis unit of claim 31 in which said cooling means comprises at least one cooling fan disposed adjacent a side of said casing enclosed space positioned such and operable to flow a stream of ambient air exteriorly against said casing enclosed space.

33. The hydrolysis unit of claim 31 comprising another cooling fan disposed at a side of the casing enclosed space opposite that of said first-mentioned casing side.

34. The hydrolysis unit of claim 1 further comprising means for cooling the specimen holder and said cover upon completion of a specimen hydrolyzing cycle.

35. The hydrolysis unit of claim 34 in which said cooling means includes a source of pressurized gas, said casing enclosed space embodying gas inflow means connected with said source, said gas inflow means being positioned to direct gas flow exteriorly onto said specimen holder and said cover.

36. The hydrolysis unit of claim 35 in which said pressurized gas source is a source of compressed air.

37. The hydrolysis unit of claim 35 in which said pressurized gas source is a source of an inert gas.

38. The hydrolysis unit of claim 37 in which the inert gas is nitrogen.

39. The hydrolysis unit of claim 34 in which the cooling means includes structure at the underside of said lower casing part for admitting a stream of cooling fluid into the casing enclosed space at a location below said specimen holder and isolated from the casing enclosed space.

40. The hydrolysis unit of claim 1 further comprising a microprocessor control unit for controlling operation of unit operating components.

41. The hydrolysis unit of claim 40 further comprising uninterrupted electrical power supply means connected with said microprocessor control unit to sustain operation of said microprocessor control unit upon happening of a main electrical power failure.

* * * * *